United States Patent [19]

Breda et al.

[11] 4,348,528
[45] Sep. 7, 1982

[54] PROCESS FOR THE PREPARATION OF 1-PHENYL-3-CARBAMOYL-5-PYRAZO-LONES

[75] Inventors: Antoine G. L. J. Breda, Craponne; Jacques G. R. Roussel, Bosc Roger en Roumois, both of France

[73] Assignee: P C U K Produits Chimiques Ugine Kuhlmann, Courbevoie, France

[21] Appl. No.: 282,903

[22] Filed: Jul. 13, 1981

[30] Foreign Application Priority Data

Jul. 18, 1980 [FR] France ............................. 80 15878

[51] Int. Cl.$^3$ ........................................ C07D 231/22
[52] U.S. Cl. .................................................. 548/367
[58] Field of Search ........................................ 548/367

[56] References Cited

U.S. PATENT DOCUMENTS 2,153,615  4/1939  Dahlen et al. ................... 548/367
2,459,226  1/1949  Kendall et al. .................. 548/367
2,659,720  11/1953 Kuster ............................. 548/367

FOREIGN PATENT DOCUMENTS 944617  4/1949  France .
313376  5/1956  Switzerland .

OTHER PUBLICATIONS

Beilsteins Handbuch der Organischen Chemie, 4th Editn., vol. 25, 1936, (Springer, Berlin), pp. 204–218.
Weissberger et al., J. Am. Chem. Soc., 1942, vol. 64, pp. 2133–2136.

Primary Examiner—Henry R. Jiles
Assistant Examiner—N. Harkaway
Attorney, Agent, or Firm—Beveridge, DeGrandi & Kline

[57] ABSTRACT

The invention relates to the preparation of 1-phenyl-3-carbamoyl-5-pyrazolones of the formula:

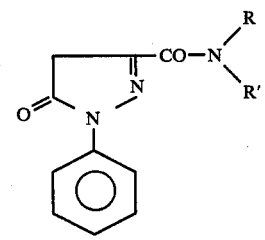

in which the two symbols R and R' may be the same or different and each represents a hydrogen atom, an alkyl radical or a substituted alkyl radical containing 1 to 4 carbon atoms.

An aqueous paste of diethyl oxalacetate phenylhydrazone is heated at a temperature not greater than 85° C. until the hydrazone is completely melted, and the aqueous phase is then removed and the remaining hydrazone is treated with 2 to 12 molar equivalents of a compound of the formula HNRR' at a temperature between 20° and 100° C. The formation of 1-phenyl-3-carboxy-5-pyrazolone is thus avoided.

4 Claims, No Drawings

PROCESS FOR THE PREPARATION OF 1-PHENYL-3-CARBAMOYL-5-PYRAZOLONES

The present invention relates to the preparation of 1-phenyl-3-carbamoyl-5-pyrazolones of the general formula:

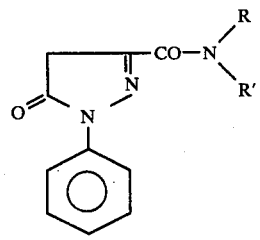

in which the two symbols R and R' may be the same or different and each represents a hydrogen atom, an alkyl radical containing 1 to 4 carbon atoms or said alkyl radical substituted, for example, by a hydroxy group.

These known compounds, used as coupling compounds for the preparation of monoazo dispersion dyes for hydrophobic fibers or for that of chromiferous complex dyestuffs for fibers of natural or synthetic polyamides, are usually prepared by condensation of phenylhydrazine with diethyl oxalacetate, cyclization of the hydrazone formed to 1-phenyl-3-carbethoxy-5-pyrazolone and formation of the amide, according to the following reaction scheme:

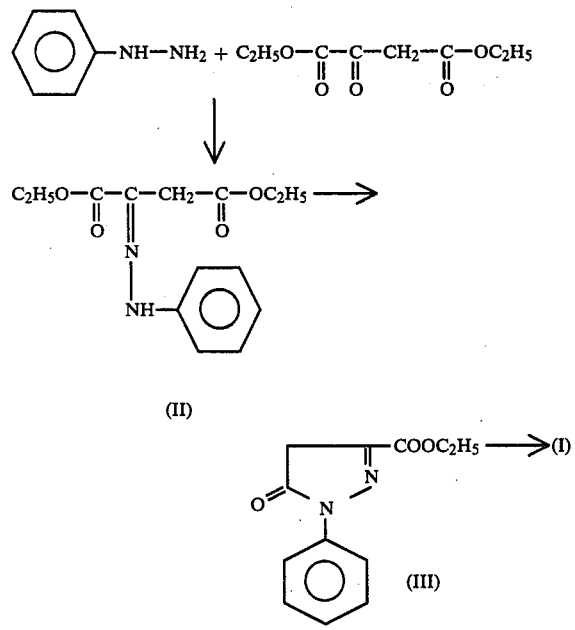

However, this method of preparation has several disadvantages in industrial practice. In fact, from the aqueous pastes of 1-phenyl-3-carbethoxy-5-pyrazolone (III), a partial hydrolysis of the carbethoxy group to a carboxy group cannot be avoided during the formation of the amide, which is prejudicial to the yield and to the quality of the final product. On the other hand, the reactions are effected in several stages with intermediate isolations which are prejudicial to the yield and to productivity.

It has now been found that partial hydrolysis of the carbethoxy group, that is the formation of 1-phenyl-3-carboxy-5-pyrazolone, can be minimized and that, in a single apparatus, a practically pure 1-phenyl-3-carbamoyl-5-pyrazolone of formula (I) can be obtained if an aqueous paste of the hydrazone of formula (II) is heated at a temperature not greater than 85° C., preferably 80° C., until the hydrazone is completely melted, then the aqueous phase is eliminated and the remaining anhydrous hydrazone is treated with 2 to 12 molar equivalents of a compound of the formula:

where R and R' have the same significance as above, at a temperature between 20° and 100° C., preferably between 80° and 90° C.

The heating of the aqueous paste of hydrazone of formula (II), possibly diluted with water, causes a separation of the reaction mixture into two phases, the molten hydrazone constituting the lower layer. If for reasons of convenience it is desired to remove the aqueous phase via the bottom of the reactor, it is sufficient to add to the reaction mixture an amount of salt (for example sodium or potassium chloride) sufficient to cause an inversion of the phases.

The cyclization of the hydrazone of formula (II) to 1-phenyl-3-carbethoxy-5-pyrazolone of formula (III) and the formation of the amide of the latter to 1-phenyl-3-carbamoyl-5-pyrazolone of formula (I) are realized in practice in a single stage during treatment by the compound of formula (IV). In order to prevent a solidification during this treatment, the reaction mixture may be diluted with an alcohol before or during the treatment. Suitable alcohols include more particularly methanol and ethanol.

When the reaction is finished, water may be added which, after elimination of the alcohol, enables the pyrazolone of formula (I) which has precipitated to be filtered if desired; an alkali such as sodium hydroxide or potassium hydroxide may also be advantageously added to the aqueous suspension so as to solubilize the pyrazolone of formula (I), the solution obtained being directly usable for the subsequent manufacture of azo dyestuffs.

With certain liquid amines of formula (IV), especially monoethanolamine, it is not necessary to dilute with alcohol; in this case however it is advisable to use at least 3 molar equivalents of amine.

The following exmples illustrate the invention without it being limited thereto. The parts and percentages indicated are by weight unless the contrary is stated.

EXAMPLE 1

1000 parts of water, then 4000 parts of an aqueous paste of diethyl oxalacetate phenylhydrazone containing about 44% of dry matter or solids and 1347 parts of pure hydrazone are charged into a vitrified steel reactor having a capacity of 7000 parts by volume. Then 750 parts of sodium chloride are added in order to adjust the density of the aqueous phase to about 1.18 and the mixture is heated at 80° C. until the supernatant hydrazone has completely melted, then the salted aqueous phase is removed.

1050 parts of monoethanolamine are run into the remaining anhydrous hydrazone, maintained at between 70° and 80° C.; since the reaction is exothermic, introduction of monoethanolamine is regulated so that the temperature remains below 85° C. When the introduction of monoethanolamine is finished, the mixture is progressively heated while the ethyl alcohol formed is distilled; the temperature of the reaction mass at the end of the distillation must not exceed 110° C.

2280 parts are obtained of a viscous liquid containing 1185 parts of 1-phenyl-N-(β-hydroxyethyl)-3-carbamoyl-5-pyrazolone. This viscous liquid may be diluted with water if desired and can be directly used for the manufacture of azo dyestuffs.

EXAMPLE 2

The operation is as in Example 1 with the exception that the monoethanolamine is replaced by 1 696 parts of diethanolamine. A viscous liquid is obtained which contains 1 367 parts of 1-phenyl-N,N-bis(β-hydroxyethyl)-3-carbamoyl-5-pyrazolone.

What is claimed is:

1. A process for the preparation of a 1-phenyl-3-carbamoyl-5-pyrazolone of the formula:

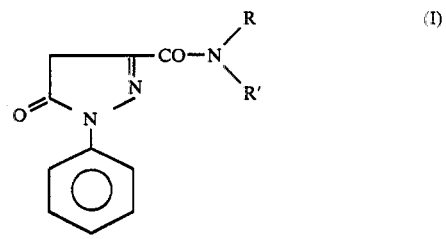

in which the two symbols R and R' may be the same or different and each represents a hydrogen atom, an alkyl radical or substituted alkyl radical containing 1 to 4 carbon atoms in which an aqueous paste of diethyl oxalacetate phenylhydrazone is heated at a temperature not greater than 85° C. until the hydrazone is completely melted, then the aqueous phase is removed and the remaining hydrazone is treated with 2 to 12 molar equivalents of a compound of the formula:

wherein R and R' have the same significance as above, at a temperature between 20° and 100° C.

2. A process according to claim 1 in which the final treatment is effected at a temperature between 80° and 90° C.

3. A process according to claim 1 or 2 in which the final treatment is effected with addition of an alcohol to the reaction mixture.

4. A process according to claim 1 or 2 for the preparation of 1-phenyl-N-(β-hydroxyethyl)-3-carbamoyl-5-pyrazolone, in which the compound of formula (IV) is monoethanolamine used at the rate of at least 3 molar equivalents.

* * * * *